(12) United States Patent
Bjork et al.

(10) Patent No.: US 10,905,565 B2
(45) Date of Patent: Feb. 2, 2021

(54) OBLIQUE INSERTER

(71) Applicant: Spineology Inc., St. Paul, MN (US)

(72) Inventors: Todd Bjork, Hudson, WI (US); Lauren Berger Vanbeek, St. Paul, MN (US); Adam Shinbrot, Woodbury, MN (US); Steve Jacobson, Lake Elmo, MN (US)

(73) Assignee: Spineology Inc., St. Paul, MN (US)

( * ) Notice: Subject to any disclaimer, the term of this patent is extended or adjusted under 35 U.S.C. 154(b) by 47 days.

(21) Appl. No.: 16/104,118

(22) Filed: Aug. 16, 2018

(65) Prior Publication Data

US 2019/0053916 A1    Feb. 21, 2019

Related U.S. Application Data

(60) Provisional application No. 62/546,536, filed on Aug. 16, 2017.

(51) Int. Cl.
*A61F 2/46* (2006.01)
*A61F 2/30* (2006.01)
*A61F 2/44* (2006.01)

(52) U.S. Cl.
CPC ......... *A61F 2/4611* (2013.01); *A61F 2/30771* (2013.01); *A61F 2/447* (2013.01); *A61F 2/4603* (2013.01); *A61F 2002/30787* (2013.01); *A61F 2002/4625* (2013.01); *A61F 2002/4627* (2013.01); *A61F 2002/4628* (2013.01)

(58) Field of Classification Search
CPC ... A61F 2/4603; A61F 2/4611; A61F 2/30771
USPC .................................................. 606/99, 86 A
See application file for complete search history.

(56) References Cited

U.S. PATENT DOCUMENTS

2017/0281365 A1* 10/2017 Robinson .............. A61F 2/4611

* cited by examiner

*Primary Examiner* — Si Ming Ku
(74) *Attorney, Agent, or Firm* — Skaar Ulbrich Macari, P.A.

(57) ABSTRACT

An inserter includes a knob at its proximal end. The knob actuates linear motion of a slide at the distal end of the inserter. The linear motion of the slide separates two pins that project from a distal end of the inserter. The pins engage and release corresponding holes defined in the faceplate of an implant. The pins can project at an oblique angle from the longitudinal axis of the inserter. The angle of projection of each pin can be different so that a jaw-like action is provided, which securely grasps the implant via the holes in the faceplate.

19 Claims, 2 Drawing Sheets

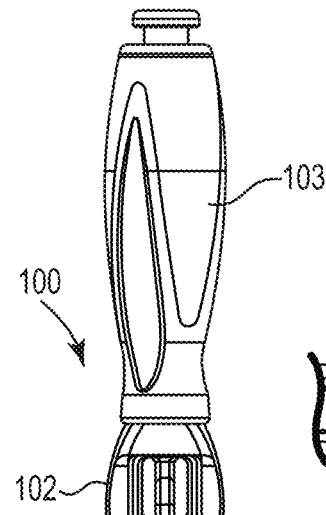
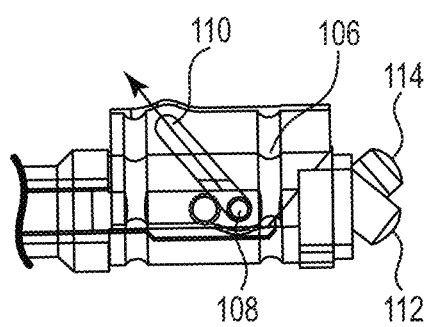
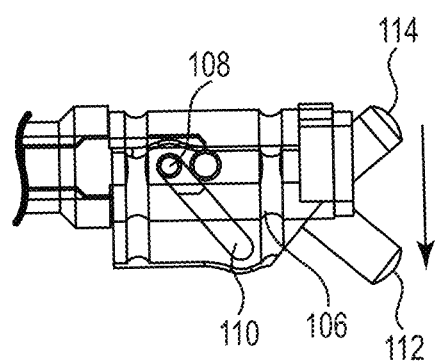
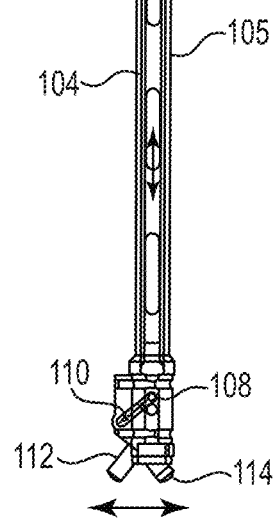
FIG. 1
FIG. 2
FIG. 3
FIG. 4

OBLIQUE INSERTER

PRIORITY

This application claims the benefit of U.S. Provisional Application Ser. No. 62/546,536, filed on Aug. 16, 2017, which is hereby incorporated herein by reference in its entirety.

FIELD

The present invention generally relates to devices used in orthopedic surgeries, and more particularly to instruments used to insert surgical implants that are implanted in orthopedic surgeries.

BACKGROUND

In surgical procedures it is desirable to minimize the surgical access opening in the patient, thereby preserving the patient's anatomy and decreasing trauma to surrounding vascular and muscular tissue. The instruments used to place implants can be bulky, requiring larger surgical access to the patient, than the implant itself would require. However, the implanting instruments need to securely grasp the implant. Thus, there is a need for an improved insertion instrument that minimizes the required surgical access opening while maintaining the implant grasping performance.

SUMMARY

The disclosure includes an insertion instrument that engages the faceplate of a surgical implant. The disclosure also includes an insertion instrument that engages and releases from screw holes in the faceplate of a surgical implant. The disclosure further includes a method of engaging an insertion instrument to a surgical implant. The disclosure additionally includes a system to insert a surgical implant.

Insertion tools are used to insert implants into patients during surgery. Often, the insertion tool engages to the outer edges of an implant. This creates a need for a larger than necessary surgical access opening, disrupting the patient's anatomy. The present invention allows the insertion tool to engage the face of the implant, such that the inserter portion that passes through the access opening is no wider than the implant.

In one of the disclosed examples, the inserter (the insertion instrument) includes a knob at its proximal end. The knob actuates linear motion of a slide at the distal end of the inserter. The linear motion of the slide separates two pins that project from a distal end of the inserter. The pins engage and release corresponding holes defined in the faceplate of an implant. The pins can project at an oblique angle from the longitudinal axis of the inserter. The angle of projection of each pin can be different so that a jaw-like action is provided.

The disclosure also includes a surgical implant insertion tool. The tool includes a slide defined at a distal end of the insertion tool, an actuator mechanically linked to the slide, a first pin disposed at the distal end of the insertion tool, and a second pin coupled to the slide. Both the first and second pins project distally from the distal end of the insertion tool. The slide is constrained to move linearly so that the second pin vertically separates from the first pin when the actuator is moved in a first direction.

The second pin can vertically contract towards the first pin when the actuator is moved in a second direction that is the opposite of the first direction. The first pin can be fixed in place so that it does not move when the slide moves. Each of the first and second pins can project laterally from the longitudinal axis of the insertion tool at an oblique angle. Each of the first and second pins can project in vertically opposite directions from one another.

The actuator can be a knob. The actuator can be mechanically linked to the slide via a shaft extending from the knob to the shaft.

A hollow tube can be disposed between the actuator and the slide, wherein the shaft extends through the hollow tube.

A handle can be disposed adjacent to the actuator.

The slide can be constrained to move perpendicular to the longitudinal axis of the insertion tool. A drive pin can travel along a slot defined in the slide.

The disclosure further includes an implant system that includes an implantable device and an insertion tool releasably securable to the implantable device. The implantable device includes a faceplate with a first and a second hole defined into the faceplate. The insertion tool includes a first pin and a second pin, each disposed at a distal end of the insertion tool. The second pin is linearly movable in a direction perpendicular to a longitudinal axis of the insertion tool. Both the first and second pins project distally from the distal end of the insertion tool. The first and second pins together secure the implantable device by grasping a respective first and second hole of the implant when the second pin is moved in a direction away from longitudinal axis of the insertion tool.

The first pin can be coupled to a slide member. The insertion tool can include an actuator to selectively move the second pin perpendicular to a longitudinal axis of the insertion tool. Each of the first and second pins can project laterally from the longitudinal axis of the insertion tool at an oblique angle. Each of the first and second pins can project in vertically opposite directions from one another.

The implantable device can be an intervertebral spacer or any other implantable body.

The distal end of the surgical implant insertion tool can have a vertical height that is less than that of the implantable device.

The disclosure still further includes a method of grasping a surgical implant with an implant insertion tool. The tool can have a vertical height that is less than that of the surgical implant. The method includes inserting a first pin of the implant insertion tool into a first hole defined into a faceplate of the surgical implant, inserting a second pin of the implant insertion tool into a second hole defined into the faceplate of the surgical implant, moving the second pin linearly away from a longitudinal axis of the implant insertion tool until the first and second pins securely grip the surgical implant. The method can further include actuating an actuator to move a slide member perpendicular to the longitudinal axis of the implant insertion tool in order to actuate the movement of the second pin moving linearly away from a longitudinal axis of the implant insertion tool.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 1 is a side view of an insertion tool according to certain embodiments.

FIG. 2 is a detailed view of the distal end portion of the insertion tool of FIG. 1 showing the pins in a retracted state.

FIG. 3 is a detailed view of the distal end portion of the insertion tool of FIG. 1 showing the pins in an extended state.

FIG. 4 is a detailed top view of the distal end portion of the insertion tool of FIG. 1.

Figure 7:
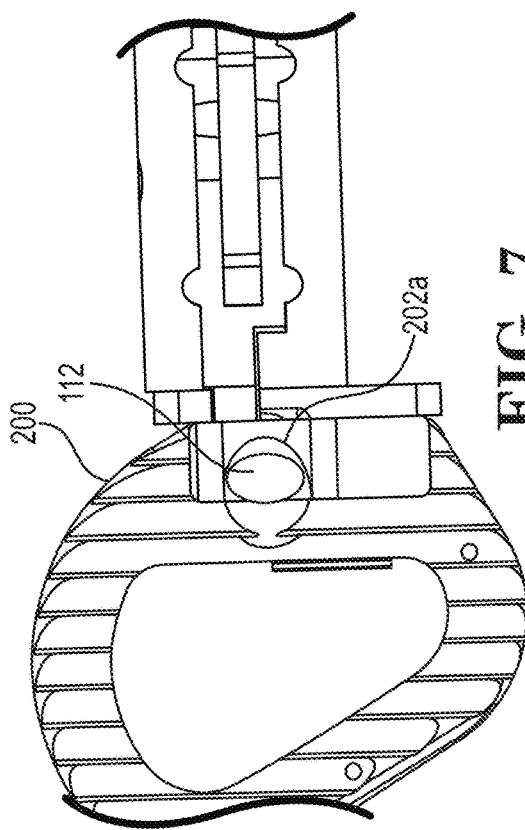
FIG. 7 is a detailed top view of a surgical implant being grasped by the insertion tool of FIG. 1 according to certain embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, dimensional relationships among individual elements in the attached drawings are illustrated only for ease of understanding, but not to limit the actual scale unless specifically claimed as such.

As is shown in FIGS. 1-4, the inserter 100 (also referred to as the insertion tool or just the tool) includes a knob 102 provided at the proximal end of the inserter. The inserter 100 is generally elongated, so it defines a longitudinal axis in its longest length direction. The knob 102 is mechanically coupled or linked via a shaft 104 to a slide 106 disposed within the distal end portion of the tool 100. The knob 102 can be threadably engaged to shaft 104.

A handle 103 can be defined adjacent to the knob 102. In one embodiment, a portion of the handle 103 is the knob. In other embodiments, such as shown in FIG. 1, the knob 102 and handle 103 are separate.

A hollow tube 105 can be provided between the handle 103 and slide 106. The shaft 104 extends through the tube 105.

Rotation of the knob 102 moves the shaft which causes vertical linear motion of the slide member 106 at the distal end of the tool 100. The motion of shaft 104 is limited by an intersecting drive pin 108 that travels along a slot 110 on slide 106. The resulting vertical linear motion of slide 106 separates two pins 112 and 114 (or jaw portions) that engage and release corresponding holes in a faceplate of an implant as will be discussed below.

Other actuators besides a rotational knob can be provided. For example, a hand-actuated trigger or handle can be provided, or other means of actuating the shaft can be provided.

In one embodiment, pin 114 is stationary. For example, it is welded in place. Thus, only pin 112 moves with slide 106. The linear actuation of center shaft 104 therefore creates a vertical reaction at the pins 112, 114 as illustrated in the transition from FIG. 2 to FIG. 3. In other embodiments, both pins can move.

In use, as knob 102 is turned, center shaft 104 advances upward or downward. Drive pin 108 intersects center shaft 104 traveling along slot 110 in slide 106. Slide 106 moves perpendicular to the longitudinal axis of the tool 100, causing pins 112, 114 to relatively move apart or closer together, depending on the direction the knob 102 is being turned.

FIG. 2 illustrates that as center shaft 104 is advanced, drive pin 108 moves along slot 110 on slide 106 (shown by arrow). As drive pin 108 travels slot 110, pins 112, 114 separate. FIG. 3 illustrates that pin 112, attached to slide 106, has moved vertically downward (shown by arrow) with respect to pin 114.

FIG. 4 illustrates pin guides 116a, 116b, 116c and 116d (see arrows). These pin guides travel along grooves defined in the tube 105 that houses the shaft 104 in order to keep slide 106 in place and prevent slide 106 from having more than one degree of freedom.

Figure 5:
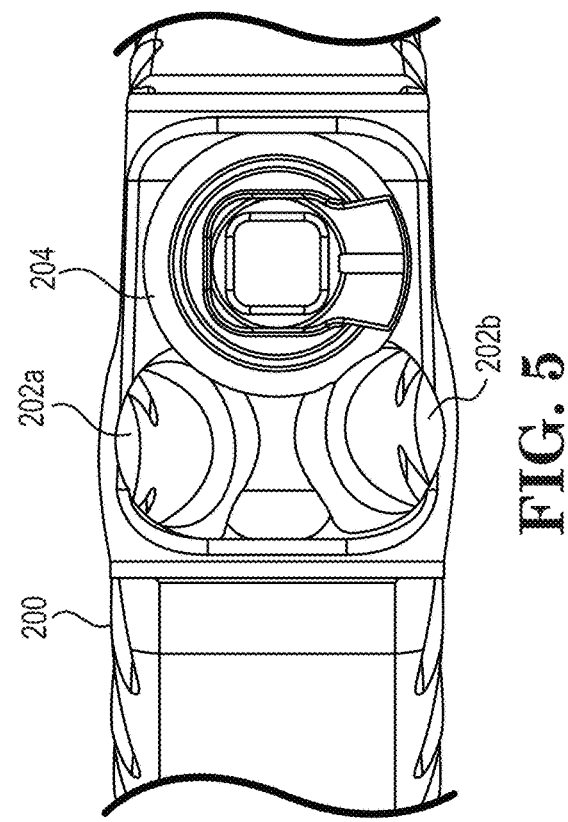
FIG. 5 is a side view of an implant having holes in a faceplate thereof to be grasped by the insertion tool of FIG. 1 according to certain embodiments.

FIG. 5 depicts an example of an implant 200 having holes 202a and 202b defined into the implant's faceplate 204. The implant 200 shown in the figures is an intervertebral spacer but other types of surgical implants can be used as well.

Figure 8:
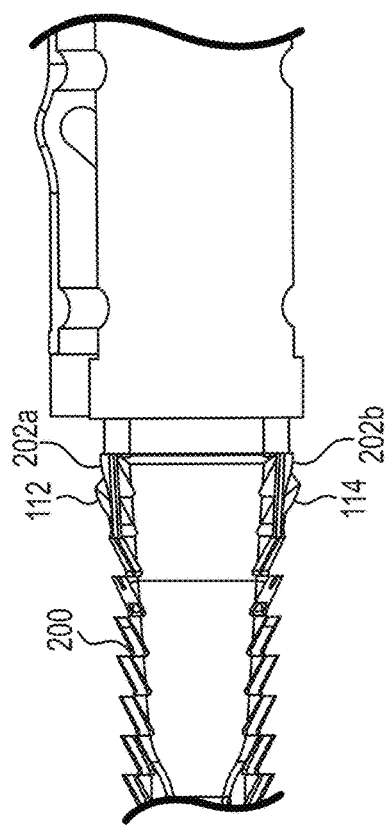
FIG. 8 is a detailed side view of a surgical implant being grasped by the insertion tool of FIG. 1 according to certain embodiments.
Figure 6:
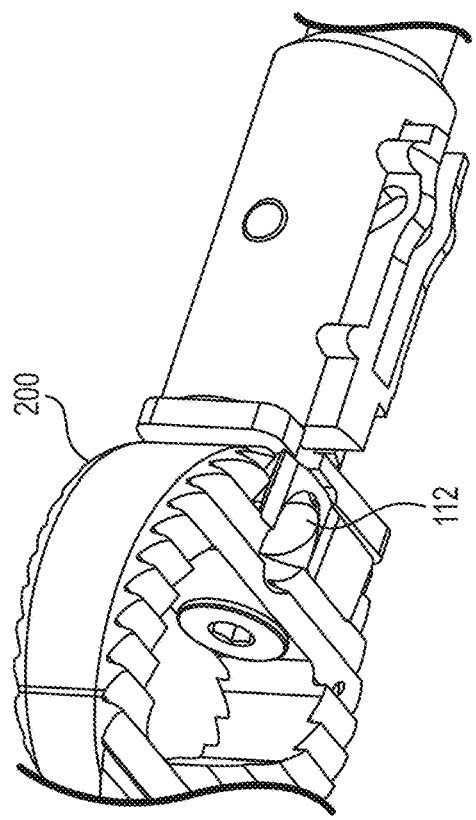
FIG. 6 is a perspective view of a surgical implant being grasped by the insertion tool of FIG. 1 according to certain embodiments.

As is shown in FIGS. 6-8, the separation of pins 112, 114 allows jaws 112, 114 to employ a tension grip on the implant due to the protrusion and separation of the pins within the holes 202 of faceplate 204.

In use, the pins 112, 114 are aligned with the respective holes in the faceplate of the implant. Then the knob 102 is turned to shift the slide 106, thereby separating the pins 112, 114, which results in the pins extending into the holes in the implant. This extension securely grasps the implant. Thus, the implant can be securely grasped with an insertion tool that can pass the distal end portion through a patient access opening that is no wider than the implant.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:
1. A surgical implant insertion tool, comprising:
   a slide defined at a distal end of the insertion tool;
   an actuator mechanically linked to the slide;
   a first pin disposed at the distal end of the insertion tool;
   a second pin coupled to the slide, wherein both the first and second pins project distally from the distal end of the insertion tool, wherein the slide is constrained to move linearly so that the second pin vertically separates from the first pin when the actuator is moved in a first direction, and wherein the first pin is fixed in place so that it does not move when the slide moves.

2. The surgical implant insertion tool of claim 1, wherein the second pin vertically contracts towards the first pin when the actuator is moved in a second direction that is the opposite of the first direction.

3. The surgical implant insertion tool of claim 1, wherein each of the first and second pins projects laterally from a longitudinal axis of the insertion tool at an oblique angle.

4. The surgical implant insertion tool of claim 3, wherein each of the first and second pins projects in vertically opposite directions from one another.

5. The surgical implant insertion tool of claim 1, wherein the actuator is a knob.

6. The surgical implant insertion tool of claim 5, wherein the actuator is mechanically linked to the slide via a shaft extending from the knob to the shaft.

7. The surgical implant insertion tool of claim 6, further comprising a hollow tube disposed between the actuator and the slide, wherein the shaft extends through the hollow tube.

8. The surgical implant insertion tool of claim 1, further comprising a handle disposed adjacent to the actuator.

9. The surgical implant insertion tool of claim 1, wherein the slide is constrained to move perpendicular to a longitudinal axis of the insertion tool.

10. The surgical implant insertion tool of claim 1, further comprising a drive pin that travels along a slot defined in the slide.

11. An implant system, comprising:
an implantable device comprising a faceplate, wherein a first and second hole are defined into the faceplate; and
an insertion tool releasably securable to the implantable device, the insertion tool comprising:
  a first pin disposed at a distal end of the insertion tool;
  a second pin disposed at the distal end of the insertion tool, the second pin linearly movable in a direction perpendicular to a longitudinal axis of the insertion tool;
  wherein both the first and second pins project distally from the distal end of the insertion tool, and
  wherein the first and second pins together secure the implantable device to the insertion tool by grasping a respective first and second hole of the implant when the second pin is moved in a direction away from the longitudinal axis of the insertion tool.

12. The implant system of claim 11, wherein the first pin is coupled to a slide member.

13. The implant system of claim 11, wherein the insertion tool further comprises an actuator to selectively move the second pin perpendicular to the longitudinal axis of the insertion tool.

14. The surgical implant insertion tool of claim 11, wherein each of the first and second pins projects laterally from the longitudinal axis of the insertion tool at an oblique angle.

15. The surgical implant insertion tool of claim 14, wherein each of the first and second pins projects in vertically opposite directions from one another.

16. The surgical implant insertion tool of claim 11, wherein the implantable device is an intervertebral spacer.

17. The surgical implant insertion tool of claim 11, wherein the distal end of the surgical implant insertion tool has a vertical height that is less than that of the implantable device.

18. A method of grasping a surgical implant with an implant insertion tool having a vertical height that is less than that of the surgical implant, the method comprising:
inserting a first pin of the implant insertion tool into a first hole defined into a faceplate of the surgical implant;
inserting a second pin of the implant insertion tool into a second hole defined into the faceplate of the surgical implant; and
moving the second pin linearly away from a longitudinal axis of the implant insertion tool until the first and second pins securely grip the surgical implant.

19. The method of claim 18, further comprising actuating an actuator to move a slide member perpendicular to the longitudinal axis of the implant insertion tool in order to actuate the movement of the second pin moving linearly away from the longitudinal axis of the implant insertion tool.

* * * * *